United States Patent [19]

Bacus

[11] Patent Number: 5,288,477
[45] Date of Patent: Feb. 22, 1994

[54] METHOD FOR PROGNOSTICATING RESPONSE TO CANCER THERAPY

[75] Inventor: Sarah S. Bacus, Hinsdale, Ill.

[73] Assignee: Becton, Dickinson and Company, Franklin Lakes, N.J.

[21] Appl. No.: 32,529

[22] Filed: Mar. 15, 1993

Related U.S. Application Data

[63] Continuation of Ser. No. 767,041, Sep. 27, 1991, abandoned.

[51] Int. Cl.$^5$ .................. G01N 1/00; G01N 33/48; G01N 33/566; C12Q 1/68
[52] U.S. Cl. ............................ 424/2; 424/85.5; 435/7.1; 436/501
[58] Field of Search .............. 424/2, 85.8; 435/7.1; 436/501

[56] References Cited

U.S. PATENT DOCUMENTS

| | | | |
|---|---|---|---|
| 4,786,590 | 11/1988 | McGrath et al. | 436/519 |
| 4,968,603 | 11/1990 | Slamon et al. | 436/94 |
| 4,998,284 | 3/1991 | Bacus | 382/6 |
| 5,008,185 | 4/1991 | Bacus | 435/7.23 |
| 5,016,283 | 5/1991 | Bacus | 382/6 |
| 5,018,209 | 5/1991 | Bacus | 382/6 |
| 5,068,175 | 11/1991 | Prashad | 436/64 |

OTHER PUBLICATIONS

Lupu et al., Science, 249:1552 (1990).
Bacus et al., Arch. Pathol. Lab. Med., 114:164 (1990).
Bacus et al., AM. J. Pathol., 137:103 (1990).
Bacus et al., Molec. Carc., 3:350 (1990).

*Primary Examiner*—Nathan M. Nutter
*Attorney, Agent, or Firm*—Robert M. Hallenbeck

[57] ABSTRACT

A method for prognosticating the effectiveness of a chemotherapy using monoclonal antibodies and ligand molecules. The putative anti-cancer agent has binding specificity for a oncogenic receptor molecule on the membrane of a cancer cell, such as HER-2/neu. When the putative agent binds to the oncogenic receptor, the receptor translocates from the membrane to the cytoplasm or perinucleus of the cancer cell, accompanied by a transient increase in the total cellular content of the receptor, and results in terminal cell differentiation. The efficacy of the agent in vivo can be determined in vitro by treatment of biopsied cancer cells with the agent and subsequent examination of the cells for evidence of terminal cell differentiation. Such evidence includes morphological change, reduction in cell growth, or production of chemicals associated with the mature phenotype. Additionally, treated cells may be examined with immunohistochemicals specific for the oncogenic receptor, to determine translocation of the receptor from the membrane to the cytoplasm or perinucleus. Quantification of receptor levels in treated cells by measuring optical densities after staining can be used to determine translocation, as well as a transient increase in total cellular content of the receptor.

17 Claims, 2 Drawing Sheets

METHOD FOR PROGNOSTICATING RESPONSE TO CANCER THERAPY

This application is a continuation of application Ser. No. 07/767,041, filed Sep. 27, 1991, now abandoned.

TECHNICAL FIELD

This invention relates generally to methods for selecting putative anti-cancer agents and for determining the efficacy of a putative anti-cancer agent useful in the treatment of a cancer characterized by expression of a surface oncogene product.

BACKGROUND OF THE INVENTION

The transformation of a normal cell into a malignant cell characteristically results, among other things, in the uncontrolled proliferation of the progeny cells, which exhibit immature, undifferentiated morphology, and expression or overexpression of oncogenes not normally expressed by normal, mature cells. It is the goal of cancer therapy to selectively kill or inhibit the uncontrolled growth of such malignant cells, while not adversely affecting normal cells.

Traditional chemotherapeutic agents are highly cytotoxic agents which preferably have greater affinity for malignant cells than normal cells or at least preferentially affect malignant cells based on their high rate of metabolic activity. Where an oncogene product unique to a malignant cell is expressed or overexpressed on its surface membrane, it may be used to target such malignant cells for destruction using chemotherapeutic agents designed to specifically interact with the oncogene product. Extremely precise methods of targeting malignant cells for destruction have become available with the advent of cytotoxic conjugates, consisting of a potent cytotoxin chemically linked to an affinity molecule such as a monoclonal antibody having specificity for a unique protein produced by a malignant cell. Using immunocytochemical and molecular analyses, it is possible to precisely identify the composition and structure of an oncogenic protein and produce a monoclonal antibody which has the capacity to specifically bind the oncogenic protein and thus, increase the accuracy of delivering the cytotoxin to the intended target cell.

Besides cytotoxic conjugates comprising an antibody as an affinity molecule for delivering a toxin linked thereto, it has been proposed to use monoclonal antibodies which are able to specifically bind to the surface of a cancerous cell. Anti-tumor effects of monoclonal antibodies may be achieved through the effector junction of the antibody molecule through natural immunological response to the antigen-antibody complex. In this respect, certain monoclonal antibodies have been shown to result in a reduction of tumor size. Undesirably, however, other monoclonal antibodies which specifically bind to such antigens on the surface of the malignant cell have no effect or, worse, actually accelerate the growth of the malignancy, even though such antibodies are specific for the same malignant cell type and the same oncogene product as the antibodies which reduce tumor size. In view of the unpredictability of the effect, if any, of an antibody on malignant cells, it has not been possible to determine, prior to starting therapy, whether one or more selected antibodies would be active as anti-tumor agents or to render an accurate prognosis. Heretofore, it has not been possible to determine which antibody preparations, of a selection of monoclonal antibodies (each of which is capable of specifically binding an oncogenic protein) are tumor antagonists, and which are tumor agonists that may undesirably accelerate proliferation of the malignancy. It would be extremely desirable to be able to determine in an in vitro assay method which antibody preparation (or combination of antibodies) having specific affinity for an oncogenic product, and how much thereof, would be predicted to inhibit the proliferation of malignant cells and provide a good prognosis for the patient. It would be very desirable to provide an in vitro method for prognosticating the efficacy of a proposed therapeutic agent (or combination of agents) and dosage thereof, which method is time- and cost-effective, as well as minimally traumatic to a cancer patient, so that the method may be practically employed in the great variety of cancer cases to be found among different patients.

SUMMARY OF THE INVENTION

I have discovered that in cancers characterized by the presence of malignant cells which express or overexpress one or more membrane-associated, receptor-like oncogenic proteins, malignant cells can be induced to terminally differentiate by administering an effective amount of a composition comprising an affinity molecule such as a monoclonal antibody which is specific for an epitope on the extracellular domain of the oncogenic protein and/or a ligand which is specific for the oncogenic protein. In preferred embodiments of the present invention, the malignancy is one that is characterized by the expression or overexpression of at least the HER-2/neu oncogene. Among the cancers which characteristically express or overexpress HER-2/neu are certain breast cancers, stomach cancers, ovarian cancers and salivary gland cancers.

Thus, a method of the present invention entails a method for determining/prognosticating the effectiveness of a therapeutic agent in the treatment of a cancer wherein malignant cells of the cancer express or overexpress an oncogene product, the method comprising the steps of: (a) obtaining viable malignant cells which express or overexpress at least one oncogene product and dividing the same into first and second portions; (b) treating the first portion comprising viable malignant cells with a sufficient quantity of a composition comprising at least one compound having specific binding affinity for the oncogene product and contacting the second portion with a composition which is devoid of the compound or compounds having specific binding affinity for the oncogene product and incubating the first and second portions in a physiologically acceptable medium for an amount of time sufficient to induce a percentage of the viable malignant cells of said first portion to terminally differentiate; and (c) comparing the percentage of cells in the first portion which exhibit morphological evidence of said terminal differentiation to the percentage of cells in the second portion which exhibit morphological evidence of terminal differentiation, or, alternatively, comparing the average value across the first portion of a parameter indicative of terminal differentiation with the average value of the parameter across the second portion. The viable malignant cells may be obtained as a tissue biopsy from a patient suffering from a malignancy in which case a therapeutic agent tailored to the patient may be selected. Alternatively, the malignant cells may be those of an established transformed cell line derived from a malignant tissue, in which case the method of the present invention may be used as a general screening assay for selecting anti-cancer therapeutic agents effective against such malignancy.

In accordance with certain aspects of the present invention, induction of terminal cell differentiation in malignant cells expressing or overexpressing HER-2/neu may be shown by an increased percentage of treated cells which express mature phenotype. For example, in the case of breast cancer, induction of differentiation in accordance with the present method may be determined by the presence of milk components such as casein and lipid droplets in the treated cells.

It has surprisingly been found that a tissue comprising malignant cells which express or overexpress HER-2/neu, when treated with an affinity molecule which has specific binding affinity for the extracellular domain of the HER-2/neu proto-oncogene product, results in terminal cell differentiation (exhibits mature phenotype) and that this differentiation is correlated to translocation of the HER-2/neu gene product from the surface membrane of a malignant cell to the cytoplasm or perinuclear region of the cell, and to a transient increase in the overall HER-2/neu content of the cell, after which translocation the cell ceases to proliferate at rates characteristic of malignant cells. Thus, a monoclonal antibody preparation useful for the treatment of a malignancy characterized by HER-2/neu expression (or overexpression) may be selected based on its ability in a method of the invention to induce in such malignant cells, translocation of HER-2/neu protein or the expression of other mature cell phenotypes as discussed below.

Additionally, I have surprisingly found that, in at least some cancers characterized by the expression or overexpression of a membrane-associated, receptor-like oncogenic protein, contacting such malignant cells with a ligand specific for the membrane-associated protein results in the induction of terminal cell differentiation and consequently the appearance in such cells of mature phenotype. In preferred aspects of the invention, the malignant cells express or overexpress the HER-2/neu gene product and the ligand specific for the gene product is the glycoprotein gp30.

Thus, the present invention entails methods for selecting anti-cancer therapeutic agents, particularly monoclonal antibodies and ligands and prognosticating the in vivo response to cancer therapy. A detectable increase in terminal cell differentiation in malignant cells, e.g., from a biopsy treated according to the method of the present invention represents potential effectiveness of the composition in cancer therapy and provides a prognostic measure of the potential effectiveness of the therapy in vivo.

DESCRIPTION OF THE PREFERRED EMBODIMENT

Figure 1:
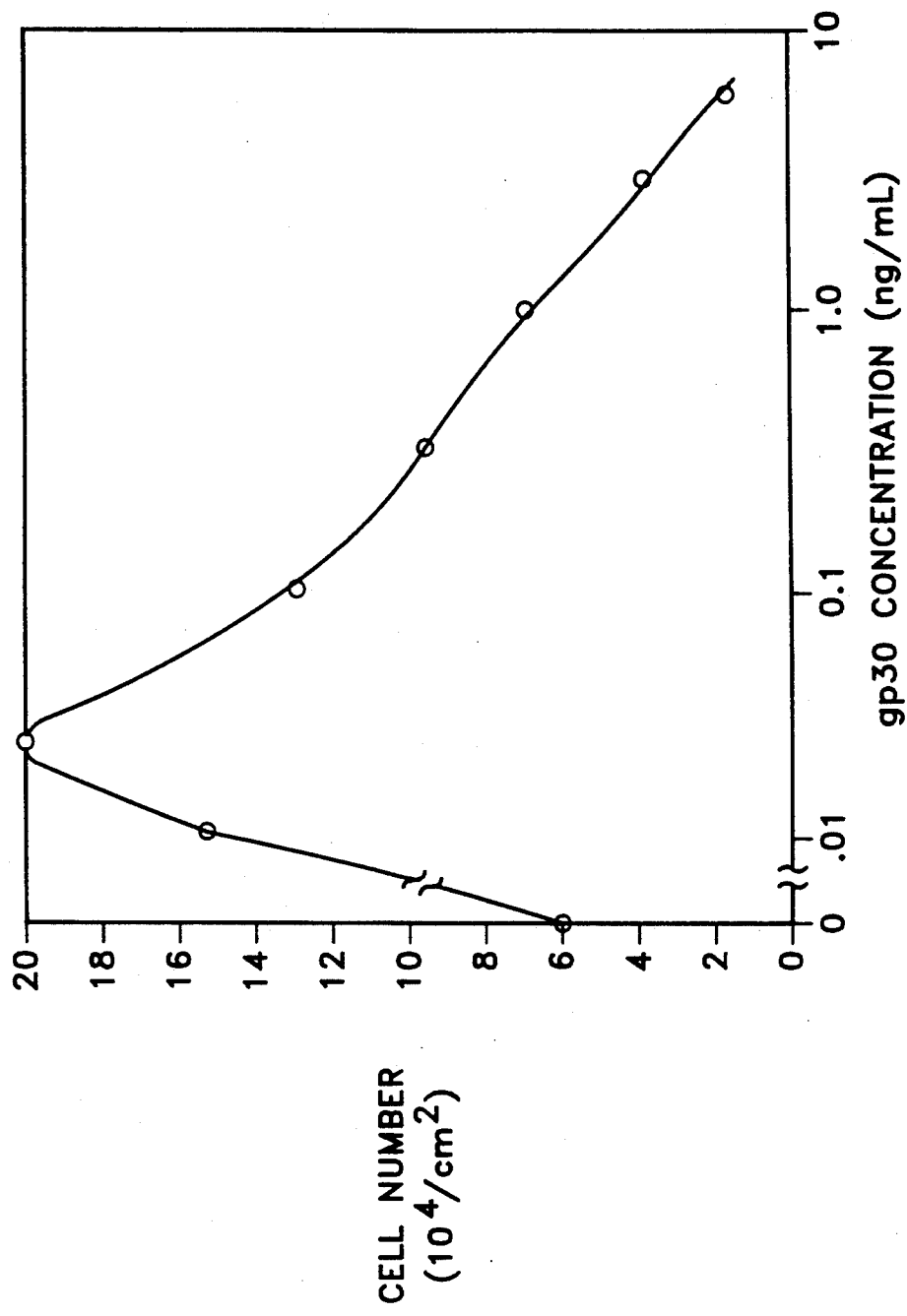
FIG. 1 shows a graph of AU-565 cell numbers per square centimeter after six days of treatment with various concentrations of ligand gp30.

In accordance with the present invention, it has been discovered that certain affinity molecules which are capable of specifically binding to the extracellular domain of receptor-like oncogene products, particularly the HER-2/neu oncogene product (also referred to herein as "HER-2/neu receptor"), have the capacity to induce malignant cells which express or overexpress the oncogene to terminally differentiate and cease unregulated proliferation. The HER-2/neu oncogene is a member of the c-erbB oncogene family. Administering such affinity molecules to a patient suffering from a malignancy characterized by expression or overexpression of such a receptor-like oncogene product may be used therapeutically, alone or in conjunction with other therapies, to treat patients suffering from such a malignant disease.

In one of its aspects, the present invention entails a method for determining/prognosticating the effectiveness of a therapeutic agent in the treatment of a cancer characterized by the expression or overexpression of an oncogene product, the method comprising the steps of: (a) obtaining viable malignant cells which express or overexpress at least one oncogene product and dividing the same into first and second portions; (b) treating the first portion comprising viable malignant cells with a sufficient quantity of a composition comprising at least one compound having specific binding affinity for the oncogene product and contacting the second portion with a composition which is devoid of the compound or compounds having specific binding affinity for the oncogene product and incubating the first and second portions in a physiologically acceptable medium for an amount of time sufficient to induce a percentage of the viable malignant cells of said first portion to terminally differentiate; and (c) comparing the percentage of cells in the first portion which exhibit morphological evidence of said terminal differentiation maturation to the percentage of cells in the second portion which exhibit morphological evidence of terminal differentiation.

In another of its aspects, the present invention entails a method for the purpose described in the preceding paragraph, the method comprising steps (a) and (b), as described above, and further comprising a step (c) comparing a quantified parameter (such as amount of HER-2/neu on the membrane, in the cytoplasm, or in the cell overall) averaged across a sample of cells in the first portion to the quantified parameter averaged across a sample of cells in the second portion.

It has been discovered that, surprisingly, culturing malignant cells which express or overexpress HER-2/neu in the presence of certain monoclonal antibodies which have a specific binding affinity for a region of the extracellular domain of the HER-2/neu receptor may cause induction of terminal cell differentiation in such malignant cells. It has also been discovered that the glycoprotein gp30 which is a ligand for the HER-2/neu receptor may similarly induce terminal cell differentiation.

In cancers characterized by the expression or overexpression of HER-2/neu, the HER-2/neu receptor is characteristically present on the surface membrane of the malignant cells, whereas normal cells and cells which have been induced to terminally differentiate in accordance with the present invention are essentially devoid of HER-2/neu on the surface membrane.

Among the indications of terminal cell differentiation are the translocation of the HER-2/neu receptor from the surface membrane to the cytoplasm or perinuclear region of the cell, and a transient increase in the total cellular amount of HER-2/neu. By "translocation of the HER-2/neu receptor" is meant that cells which have been induced to terminally differentiate have substantially reduced amounts of HER-2/neu receptor on their surface membrane and transiently increased amounts of HER-2/neu receptor or a portion thereof present in the cytoplasm or perinuclear region of the cell. Thus, in accordance with methods of the present invention, a prognostic determination of the effectiveness of a cancer therapy utilizing a selected monoclonal antibody or ligand may be made by maintaining a biopsy of cancerous tissue in the presence and absence of an affinity molecule having such putative therapeutic effect and determining whether the tissue maintained in the presence of the affinity molecule has an increased percentage of cells which exhibit translocation of HER-2/neu or other indications of terminal cell differentiation as compared to the percentage of similarly obtained cells which were maintained in the absence of the affinity molecule, or alternatively whether the tissue maintained in the presence of the affinity molecule has a decreased amount of membrane-bound HER-2/neu or an increased amount of cytoplasmic or total cellular HER-2/neu averaged over a sample of cells compared to the same parameter averaged over a sample of cells which were maintained in the absence of the affinity molecule. The method of the present invention may be employed advantageously to determine the efficacy of an affinity molecule at various concentrations or a combination of affinity molecules, for example, a composition comprising at least two monoclonal antibodies and/or ligands (at one or more concentrations) which individually are capable of inducing terminal differentiation in such malignant cells.

In accordance with the present invention as it pertains to in vitro assay methods for selecting, or determining the efficacy of, an affinity molecule which is capable of causing induction of terminal differentiation in a malignant cell of a patient suffering from the malignancy, a biopsy is obtained, as well known to those skilled in the art, of a cancerous tissue having such malignant cells which express or overexpress HER-2/neu receptor.

Preferably a biopsy will be obtained which is suitably sized so that it may be divided into a plurality of portions for testing with one or more putative agents, at one or more concentrations. While the biopsy may be maintained for up to several days in a suitable maintenance medium, as well known in the art, it is preferred to employ a biopsied tissue sample in accordance with the present invention within about 24 hours or less from the time it is excised.

The tissue biopsy may be divided into a suitable number of representative pieces and one or more of the pieces placed in individual sterile culture vessels (e.g., separate wells of a microtiter plate). The number of pieces of biopsied tissue that are employed in an assay will be determined by the number of compounds and concentration thereof which are tested. Also, however, it is contemplated to mince or otherwise disperse the tissue biopsy so that the cells can be cultured, as known in the art, to provide a suitable number of culture vessels having viable malignant cells grown from the biopsy as primary cultures. In this way the number of malignant cells obtainable for use in an assay method of the invention may be multiplied. It is preferred to have at least one aliquot of the biopsied tissue (or cells thereof) as a negative control which is not contacted with a putative anti-cancer compound so that the percentage of cells exhibiting evidence of terminal cell differentiation in the absence of the putative compound(s) may be determined.

In accordance with the present invention a monoclonal antibody or ligand or a combination of these affinity molecules may be added to the cultured biopsy comprising malignant cells after seeding; it is preferred to allow the biopsied tissue segments to acclimate to culture conditions for about one day after seeding and then add the putative agents to the respective cultures in an amount which is sufficient to give a predetermined concentration of the agent. Alternatively, a series of tubes of culture media, each of which is supplemented with a predetermined amount of one or more putative agents, may be used to seed the cells directly into the culture vessel.

The individually treated aliquots of the biopsied material are then incubated for a period of time sufficient to cause induction of terminal cell differentiation in at least a portion of the malignant cells of the biopsied material. Generally a statistically significant percentage of cells (as compared to a negative control) exhibit evidence of terminal cell differentiation within about one to about seven days of incubation in the presence of a compound which has the capacity to induce differentiation. Conventional incubation conditions for human and other mammalian cells are well known in the art. Suitable incubation conditions include an incubation temperature of about 20°–45° C., more preferably about 33° C.–39° C., most preferably about 37° C., and a humidified atmosphere of air supplemented with about 5%–10% $CO_2$. Where incubation times employed in the assay methods of the invention exceed about 3 or more days, it may be desirable to exchange the spent culture medium in the respective vessels for fresh culture medium, preferably supplemented with the same concentration of the putative agent.

While it is preferred to tailor the selection of affinity molecules for use as anti-cancer agents to individual patients by employing a biopsied tissue segment from such patient in an assay method of the invention, the present invention also includes screening methods for determining the efficacy of affinity molecules such as monoclonal antibodies or ligands having specificity for the HER-2/neu receptor wherein cells of a transformed cell lines are used instead of fresh biopsied tissue. Examples 1 and 2 describe induction of terminal cell differentiation induced by incubating cells of well-known, readily obtainable transformed cell lines with monoclonal antibody preparations which are specific for a portion of the extracellular domain of the HER-2/neu receptor.

Monoclonal antibodies which have specific binding affinity for certain regions on the extracellular domain of the HER-2/neu receptor are one type of affinity molecules which are capable of inducing malignant cells expressing or overexpressing HER-2/neu to undergo terminal cell differentiation. Importantly, it is a necessary, but not sufficient, condition that a monoclonal antibody be specific for an epitope on the extracellular domain of the HER-2/neu receptor. In other words, not all monoclonal antibodies which are able to specifically bind a region of the extracellular domain of HER-2/neu are able to induce differentiation. Some monoclonal antibodies that meet this first criterion have no effect or, worse, may have an agonistic effect on the proliferation of such malignant cells expressing HER-2/neu, such that their administration in vivo may undesirably promote growth of the malignancy. Also, a monoclonal antibody which is capable of inducing differentiation may have such an effect in one range of concentrations, but have an opposite, agonistic effect at a different (i.e., higher or lower) concentration. Thus, the present invention provides a method for determining a preferred range of dosages of a therapeutic agent to be used in therapy.

Monoclonal antibodies which are capable of reacting with the HER-2/neu receptor are known in the art. Methods of making monoclonal antibodies generally are also well known in the art. With respect to producing monoclonal antibodies which are specific for the extracellular domain of HER-2/neu, briefly, an animal capable of producing an immune response to the antigen (e.g, HER-2/neu protein) is injected with the antigen in a manner which will result in an immune response. The antigen may be HER-2/neu receptor which has been isolated from malignant cells which produce the receptor, or the antigen may be produced by recombinant expression of the HER-2/neu gene (or a portion thereof which encodes at least a portion of the extracellular domain) transformed or transfected as known in the art into in a suitable bacterial, yeast or mammalian host cell for the production of recombinant HER-2/neu protein (or portion thereof). Monoclonal antibodies may be produced from mouse lymphocytes by injecting a mouse with a natural or synthetic protein (or part of a protein) or cell membranes derived from whole cells. The immunized animal naturally develops an immune response to the antigen and produces B-lymphocytes which produce antibodies to various epitopes of the antigen, which lymphocytes are isolated and fused with myeloma cells to form hybridomas (hybrid clones which produce a single species of antibody molecule specific for a unique epitope on the antigen). Clones with the desired antibody specificity are selected by their ability to (1) bind specifically to the extracellular domain of the HER-2/neu receptor and (2) induce terminal cell differentiation in viable malignant cells which express or overexpress HER-2/neu. Selected antibody-producing cell lines are expanded by conventional tissue culture techniques and monoclonal antibodies may be routinely purified from the culture medium. Monoclonal antibodies which fulfill criterion (1) and (2) above appear to be able to mimic the action of a ligand for the HER-2/neu receptor.

It has also been found, surprisingly, that ligands for the HER-2/neu receptor are affinity molecules which are capable of inducing malignant cells expressing or overexpressing HER-2/neu to undergo terminal cell differentiation. An especially preferred ligand for use in the method of the present invention is glycoprotein gp30. See, generally Lupu, R., et al., "Direct Interaction of a Ligand for the erbB2 Oncogene Product with the EGF Receptor and p185$^{erbB2}$," *Science*, Vol. 249, pp. 1552-1555 (1990), which describes the isolation and characterization of glycoprotein gp30 as a ligand for HER-2/neu receptor.

After treatment of the biopsy portions or cell cultures, the portions or cultures are analyzed for indicia of induced differentiation. Phenotypically, induced differentiation is evidenced by maturation markers including inhibition of cell growth, altered cytoplasmic and nuclear morphology, and, in malignant breast cells, enlargement of the nuclear size and synthesis of milk components such as casein and lipids. Surprisingly, it has been found that concomitantly with one or more of these mature phenotypic changes, the HER-2/neu protein translocates (or migrates) from the membrane to the cytoplasm and/or perinuclear regions of the cell, and that this translocation is additionally associated with a transient increase in total cellular HER-2/neu content. Translocation and a transient increase in total cellular HER-2/neu content may serve as reliable indicators of terminal cell differentiation, in accordance with the present invention.

In particularly preferred embodiments of the present invention, the response to antibody or ligand therapy in a patient having breast cancer or ovarian cancer is prognosticated by contacting a biopsied sample from said cancerous tissue with the monoclonal antibody or ligand selected for therapy for a predetermined time and determining, by immunohistochemical staining techniques which are well known in the art, translocation of the HER-2/Neu gene product from the cell membrane to the cytoplasm or perinuclear region of said cancerous cell, or a transient increase in total HER-2/neu content. Stained samples may be analyzed for optical density values which correspond to the amounts of stained cell constituents. Translocation may be determined by (1) a reduction of HER-2/neu in the surface, (2) an increase in HER-2/neu in the cytoplasm or perinuclear region, (3) a transient increase in the total HER-2/neu content, or a any combination of (1), (2) and (3).

The malignant (e.g., biopsied) cells treated in accordance with a method of the invention, in the presence or absence of a putative anti-cancer agent, are then examined to determine the percentage of cells which have been induced to differentiate. In a preferred embodiment of the invention, this is determined by comparing the percentage of treated cells containing HER-2/neu predominantly in the cytoplasm and/or perinuclear region as compared to the percentage of cells in a negative control (i.e., not treated with a putative agent) showing such a distribution of HER-2/neu protein. A decrease of HER-2/neu protein in the surface membrane of the treated cells, alone, or in combination with an increase in the cytoplasm or perinuclear region or an increase in the total HER-2/neu content (as compared to untreated cells) may be used to indicate induction of terminal differentiation.

Preferably, the average amount of membrane-bound HER-2/neu per cell in the control population can be used as a test value in obtaining cell percentages. The average is calculated from a statistically significant number of cells in the control group. Then, the amount of membrane-bound HER-2/neu in individual control group cells is compared to the average, to determine what percentage of the population has a lower amount of membrane-bound HER-2/neu, and what percentage has a higher amount. Then, cells from the treated group are similarly examined to determine what percentage of cells evidence less membrane-bound HER-2/neu than the control group average, and what percentage evidence greater membrane-bound HER-2/neu than the control group average. Finally, a comparison can be made between the percentages obtained for the control group, and the percentages obtained for the treated group. A statistically significant increase in the percentage of cells in the treated group over the percentage of cells in the control group which have less membrane-bound HER-2/neu than the control group average indicates translocation of HER-2/neu.

The amount of cytoplasmic HER-2/neu may be examined instead of the amount of membrane-bound HER-2/neu to obtain cell percentages as described above. A statistically significant increase in the percentage of cells in the treated group over the percentage of cells in the control group which have more cytoplasmic HER-2/neu than the control group average indicates translocation of HER-2/neu.

The total amount of cellular HER-2/neu may also be examined instead of membrane-bound or cytoplasmic HER-2/neu to obtain cell percentages as described above. A statistically significant increase in the percentage of cells in the treated group over the percentage of cells in the control group which have more total cellular HER-2/neu than the control group average indicates translocation of HER-2/neu.

In an alternative embodiment, the average amount of HER-2/neu found in a sample of treated cells (by examination of optical density values after staining) may be compared to the average amount of HER-2/neu found in a sample of control cells to determine translocation. The amount compared may be only that which is membrane-bound, in which case a statistically significant decrease in staining in the treated sample indicates translocation. Alternatively, the amount compared may be only cytoplasmic, or may be the total cellular content, in which cases any statistically significant increase in staining in the treated sample indicates translocation.

The expression of casein or the presence of lipid droplets may also be used as an indicator of terminal cell differentiation in malignant breast cancer cells, as discussed below.

The location and distribution of a cellular component such as HER-2/neu protein or casein or lipid droplets may be determined immunohistochemically. The cells of the biopsied sample may be fixed in a fixative, such as paraformaldehyde, followed by treatment with an organic solvent, such as acetone, formalin, or methanol, so as to render the cells permeable for immunohistological staining. Methods of fixation are well within the skill of the art.

Where the presence and distribution of HER-2/neu is to be determined, cells may be stained with an anti-HER-2/neu antibody conjugate comprising a fluorescent dye such as fluorescein, rhodamine and the like, chemically coupled to an antibody specific for the HER-2/Neu gene product without loss of antibody specificity. The location and distribution of HER-2/neu in the cells may be determined conventionally by fluorescence microscopy, and, optionally, confirmed by confocal microscope image analysis as known in the art. Besides immunofluorescence staining, other well known direct or indirect antibody staining procedures which detect the presence of specific antigen-antibody complexes such as peroxidase-anti-peroxidase staining procedures or alkaline phosphatase staining may be used to determine the distribution of HER-2/neu in such fixed cells.

Mature phenotype expression may also be used to determine the extent of terminal cell differentiation in a treated portion of biopsy. For example, immature, cancerous human breast cells and mature cells (e.g., malignant cells which were induce to differentiate) may be distinguished by the ability of the mature cells, but not the malignant cells, to produce human milk components, including casein and lipids. The percentage of cells which have been caused to differentiate in a method of the invention may be determined by the presence of such milk components. Casein may be detected by known immunohistochemical staining using anti-casein antibodies. The presence of lipids may be detected by staining with a dye compound suitable for such detection, such as Oil Red O.

After staining, the location of the HER-2/neu protein can be determined and a qualitative or quantitative analysis made of HER-2/neu migration (i.e., translocation). A quantified measure of the amount of the protein per cell can be taken by digitizing microscope images of stained samples, and converting light intensity values of pixels of the digitized image to optical density values, which correspond to the amounts of stained protein, Bacus, J. W., et al., "Optical microscope system for standardized cell measurements and analyses," *Applied Optics*, Vol. 26, pp. 3280–3293, 1987.

In particular, this quantification may be accomplished in the following manner. A cell culture sample is stained for the oncogene protein, according to a staining procedure as described above, or some other staining procedure known in the art. The cell culture sample is also stained for DNA, using a staining method known in the art, such as the Feulgen technique. The DNA stain should be distinguishable on the basis of the wavelength emitted (e.g., different colors) from the stain for the protein to permit differentiation between the two stains. Digitization of two different filtered images of the single sample image through respectively different filters, one for each specific stain, allows an optical density value to be associated with each pixel of each filtered image in a computer system programmed to process the images. The optical density of the protein stain image and the optical density of the DNA stain image are summed by the computer.

The DNA stain is applied to another sample of the same cell culture, and a human operator interactively identifies individual cells to the computer, which calculates sums of optical densities for the individual cells so identified. This second image thus supplies the average DNA per cell. The previous sum of optical density from the first DNA stain image, representing the total DNA that was seen in that image, is divided by the average DNA per cell for the culture. This yields the number of cells in the first preparation. The sum of optical density for the protein is then divided by this number of cells to yield the average protein content per cell. A reference preparation of a standard cell line, not necessarily related in any way to the cells from the biopsy, and in which DNA content and oncogene protein content per cell are known, may be stained with identical stains and used to calibrate optical density with the mass of stained material. A fuller understanding of this method of protein quantification may be obtained from U.S. Pat. No. 4,998,284 to Bacus, et al., for *Dual Color Camera Microscope and Methodology for Cell Staining and Analysis*, U.S. Pat. No. 5,008,185 to Bacus for *Methods and Apparatus for the Quantitation Of Nuclear Proteins*, U.S. Pat. No. 5,016,283 to Bacus, et al., for *Methods and Apparatus for Immunoploidy Analysis*, and U.S. Pat. No. 5,018,209 to Bacus for *Analysis Method and Apparatus for Biological Specimens*, the teachings of which are incorporated by reference into the present disclosure.

The quantification of membrane-bound HER-2/neu and cytoplasmic HER-2/neu is preferably carried out by selecting for optical density summation only those pixels in the digitized images which correspond to the membrane or the cytoplasm, or representative portions thereof, respectively. Pixel selection may be carried out by automatic computer algorithm or by human interaction.

Alternatively, membrane-bound HER-2/neu may be quantified using the above-described digitized image analysis in conjunction with fixation and staining procedures which do not make the membrane permeable to the elements of the staining complex and thus result exclusively in staining of membrane-bound HER-2/neu. Briefly, sample cells are fixed for 60 minutes at room temperature in 10% neutral buffered formalin. The murine monoclonal antibody TA-1 (IgG) (Applied Biotechnology, Inc., Cambridge, Mass.), which is directed to the membrane-external domain of HER-2/neu, is applied, typically at a concentration of 2 $\mu$g/mL. This fixation procedure does not make the cells permeable to the TA-1 antibody. Further linking antibodies and stains are applied as is known in the art, with the result that only membrane-bound HER-2/neu is stained. The amount of membrane-bound HER-2/neu per cell averaged over a sample of cells is determined as described above, by image analysis and using a Feulgen stain for the DNA.

Alternatively, indicia of terminal differentiation in cells subject to the method of the present invention include morphological changes in cells which are characteristic of a mature cell type. In cases where the morphological change is dramatic, such as a fundamental qualitative change in the shape or structure of a cell as viewed through a microscope, a determination of the extent of cell differentiation may be made by examining the cells under a microscope and counting the number of cells which exhibit qualitative morphological features associated with terminal cell differentiation. Malignant cells characteristically are compact and spherical, whereas terminally differentiated cells characteristically are flattened, having a cytoplasm which exhibits a delicate lacy appearance. The percentage of cells displaying the latter morphological features may be used to quantify the extent of terminal cell differentiation induced by a putative therapeutic agent in a given portion of biopsy and consequently permit a prognosis relating to the effect of the putative therapeutic agent in the malignancy sought to be treated.

Moreover, quantitative morphological differences, such as the change in the ratio of cytoplasmic area to nucleic area and the increase in nuclear area, which may be quantified by computerized image analysis techniques, may be used to delineate between immature and mature cells.

Cell proliferation is yet another measure of the extent of terminal cell differentiation. Immature cancerous cells will proliferate indefinitely whereas mature cells do not. A stabilization and reduction of cell population as compared to untreated control cells indicates substantial terminal cell differentiation. A marked difference in growth curves between treated and untreated portions may also indicate substantial terminal cell differentiation. Statistical methods for analyzing cell populations are well known in the art, and the aforementioned examples should not be taken as a limitation of the methods which may be applied to determine aspects of terminal cell differentiation within the cell population.

The invention is now illustrated in the following Examples.

EXAMPLE I

This Example demonstrates induction of terminal cell differentiation in malignant breast cells which overexpress HER-2/neu gene product on their cell surface by incubation of such malignant cells in the presence of monoclonal antibody having specific binding affinity for the extracellular domain of the HER-2/neu gene product.

The monoclonal antibodies to the HER-2/neu receptor were made by injecting Balb/c mice intraperitoneally 3 times (2 week intervals) with 3 to $5 \times 10^6$ viable SKBR3 human breast cancer cells. Several mice produced antisera capable of immunoprecipitating radioactively labelled HER-2/neu protein. Spleen cells of mice which developed a strong immune response were isolated and fused with NSO myeloma cells, using polyethylene glycol, and hybridomas were selected with HAT (hypoxanthine/aminopterin/thymidine) medium. The monoclonal antibody containing conditioned medium of individual hybridomas were screened for specific binding affinity for recombinant HER-2/neu receptor expressed on the surface of fixed Chinese hamster ovary cells which had been transfected with an appropriate expression vector. Monoclonal antibodies specifically binding HER-2/neu receptors were detected with $^{125}$I-labeled goat anti-mouse F(ab')$_2$ antibody. The antibodies that specifically bound to the transfected CHO cells were selected for further analysis using either an immuno-precipitation assay with [35S] methionine labeled cells, or immuno-precipitation followed by auto-phosphorylation in the presence of MnCl$_2$ and $\gamma$[$^{32}$P]ATP. This immunization procedure elicited specific antibodies to the extracellular portion of the human HER-2/neu antigen. Four of the monoclonal antibody preparations, designated N12, N24, N28 and N29, prepared as just described, were kindly provided by Dr. Yosef Yarden of the Weizmann Institute, Rehovot, Israel. Monoclonal antibodies N12, N24, N28 are of the IgG1 subclass and the N29 monoclonal antibody preparation is of the IgG2 subclass. The antibodies were diluted in phosphate buffered saline to the desired concentration, such that they could be conveniently added to culture medium.

Human breast cancer cell lines, AU-565, MDA-MB 453 and MCF-7, are well known in the art and widely available. The AU-565 cell line overexpresses both HER-2/neu and epidermal growth factor receptor; MDA-MB 453 cells overexpress HER-2/neu; MCF-7 cells do not overexpress HER-2/neu. In each case cultured cells of the respective cell lines trypsinized, pelleted and seeded into either Lab-tech four chamber slides from Nunc, Inc., Naperville, Ill., at $0.5 \times 10^4$.

The AU-565 cells (originally derived from a pleural effusion of a breast carcinoma) were obtained from Naval Biosciences Laboratory in Oakland, Calif. Cultures of MCF-7 cells (ATCC accession no. MCF-7 HTB 22) and MDA-MB 453 (ATCC accession no. 453 HTB 131) were obtained from the American Type Culture Collection in Rockville, Md.

The cells were cultured in RPMI 1640 supplemented with 20% fetal bovine serum, penicillin (100 $\mu$g/mL) and streptomycin (100 $\mu$g/mL) in a humidified incubator with 8% CO$_2$ in air at 37° Celsius. One day after seeding, when the cells were approximately 10%-20% confluent, the cell culture medium cells was supplemented with 10 $\mu$g/ml of one of the following monoclonal antibody preparation having specificity for the extracellular domain of the HER-2/neu protein: N12, N24, N28 and N29, control IgG (an unrelated IgG antibody). Also, phosphate buffered saline, alone, was added to certain control cultures as a control in which IgG was absent. The cells were cultured for an additional 4 days and then examined to determine the efficacy of the respective monoclonal antibody preparations with respect to inducing the malignant breast cells to undergo terminal cell differentiation. Differentiation was assayed by an increase in the percentage of cells producing lipid droplets, an increase in the percentage of cells producing casein, a decreased cell growth, an increase in nuclear area per cell and the translocation of HER-2/neu, as evidenced by an increase in total cellular content of the protein and human identification of the location of staining in confocal microscopy. The results shown in Table I relate to the AU-565 cell line.

toxylin, blued in saturated lithium carbonate, and covered with glycerol jelly.

The presence of casein was detected by histochemical staining with a mouse monoclonal antibody to human $\beta$ or K casein. After the medium was removed, cell slides were rinsed with phosphate-buffered saline (PBS), and the cells were fixed in ethanol-formol solution at room temperature for 10 minutes. After nonspecific binding was blocked with 20% goat serum for 20 minutes at room temperature, the cells were incubated with the anticasein ($\beta$ and K) antibody (1:250 dilution) at room temperature for 60 minutes. The slides were then rinsed with 0.5M Tris-buffered saline (TBS), pH 7.6, and then incubated with the linking antibody, biotinylated goat anti-mouse IgG (Jackson Labs, West Grove, Pa.) at a 1:200 dilution for 30 minutes. The cells were rinsed with TBS, and streptomycin conjugated alkaline phosphatase (Jackson Labs) at 1:200 dilution was applied to the

TABLE I

CELL GROWTH, DIFFERENTIATION MARKERS, AND HER-2/NEU LEVELS IN AU-565 CELLS AFTER FOUR DAYS

| Treatment | Concentration $\mu$g/ml | Cell Numbers $10^4$/cm$^2$ | Her-2/neu percent* | Nuclear Area $\mu$m$^2$ | % Cells stain for lipid droplets | % Cells stain for casein |
|---|---|---|---|---|---|---|
| Control | 0 | 6.0 | 103% | 100 | 12 | 20 |
| IgG (control) | 10 | 6.3 | 84% | 101 | 7 | 20 |
| N12 | 10 | 5.6 | 154% | 121 | 40 | >90 |
| N24 | 10 | 7.1 | 152% | 147 | 52 | >90 |
| N28 | 10 | 8.6 | 104% | 102 | 8 | <30 |
| N29 | 10 | 4.8 | 160% | 154 | 55 | >90 |

*HER-2/neu in sparsely growing untreated AU-565 = 100%

The method of the present invention indicated that monoclonal antibody N29, N24 and N12 induced the malignant breast cells to undergo differentiation and exhibit mature phenotypic traits, whereas the N28 antibody, which also has specific binding affinity for a portion of the extracellular domain of the HER-2/neu receptor, actually promoted the tumorigenicity of the treated AU-565 cells. Confocal microscope images showed that treatment of AU-565 cells with N28 antibody did not result in a translocation of the HER-2/neu protein from the membrane, while translocation from the membrane to the cytoplasm and perinuclear region of the cells was demonstrated in AU-565 cells treated with the N29, N24 and N12 monoclonal antibodies.

Results for the MDA-MB 453 cell line were similar to results for the AU-565 cell line. The MCF-7 cells, which do not overexpress HER-2/neu, were largely unaffected by the antibodies, except that monoclonal antibody N29 increased the percentage of cells exhibiting lipid droplets.

Phenotype expression as a marker of terminal cell differentiation was measured by detecting the production of lipid droplets and casein, both of which are components of human milk. Lipid droplets were detected by a modified "Oil Red O in propylene glycol" method. D. C. Sheehan, *Theory and Practice of Histotechnology*, p. 209, C. V. Mosby Company, St. Louis, (2nd ed. 1980). For the lipid staining procedure, the culture medium was removed, the cells were rinsed with 0.05M phosphate buffered saline, pH 7.6, and fixed by a quick dip in −20° Celsius methanol/acetone. After fixation, the slides on which the cells were grown were placed in absolute propylene glycol for 2 minutes at room temperature (22° Celsius) and then for 7 minutes at room temperature in an Oil Red O staining solution. The slides were then dipped in 85% isopropanol, rinsed with deionized water, counterstained in Mayer's hemacells for 30 minutes. The cells were rinsed again with TBS and incubated for 15 minutes with CAS Red (Cell Analysis Systems, Inc., Elmhurst, Ill.) as the chromogen. The cells were then counterstained with CAS DNA stain (Cell Analysis Systems, Inc., Elmhurst, Ill.).

The localization of the HER-2/neu protein (i.e., translocation of HER-2/neu) was determined using confocal microscopy after immune-fluorescence staining. For determination of translocation, after the culture media was removed and the cells were rinsed with PBS, the cells were made permeable with 95% ethanol for 10 minutes. Following a TBS rinse, the cells were postfixed in 10% neutral buffered formalin for 30 minutes. After a deionized water wash, the cells were stained for DNA with a Feulgen stain, whereupon they were rinsed well with TBS (pH 7.6). After a 20 minute block with 20% normal goat serum, one portion of the cells (the other portion served for an estimate of the average DNA content of the cells, described below) was incubated with a polyclonal antibody to the C terminus of the HER-2/neu protein (Oncogene Kit from Cell Analysis Systems, Inc., Elmhurst, Ill.) for 60 minutes at room temperature. The cells were then rinsed with TBS, and incubated with a first linking antibody, mouse anti-rabbit IgG at a protein concentration of 10 mg/L (Jackson Laboratories, West Grove, Pa.) for 30 minutes. Then dichlorotriazinyl amino fluorescein [DTAF]-conjugated goat anti-mouse IgG (Jackson Labs) was applied at a dilution of 1:100 for 30 minutes at room temperature. The cells were then rinsed with TBS, and coverslipped with gelvatol. Localization was determined using a Bio/Rad MRC-600 confocal scanning microscope adapted with a fluorescein filter. Confocal optical sections were recorded at 1$\mu$ intervals with 10 times averaging per image.

A CAS 200 Image Analyzer (Cell Analysis Systems, Inc., Elmhurst, Ill.), a microscope-based, two color image analyzing system, was used in the quantification of the HER-2/neu protein. Both solid state imaging channels of the CAS 200 Image Analyzer were used. Digitized light intensity values were converted to optical density values and added together, the result corresponding by the Lambert-Beer Absorption Law to the amounts of stained cell constituents. The two imaging channels were specifically matched to the two components of the stains used. One channel was used for quantifying the total DNA of the cells in the field following Feulgen staining with a DNA staining kit and the other for quantifying the total HER-2/neu protein of the cells in the field following immunostaining.

A separate preparation of cells from the same culture (the other portion mentioned above) was stained only for DNA. A human operator identified individual cells to the apparatus, and optical densities of the pixels associated with each cell were summed. Summed optical densities for each cell as well as a count of the number of cells were produced. This supplied the total DNA amount per cell for the culture.

Since the total DNA amount per cell was known from this second sample, the average total HER-2/neu protein per cell could be computed from the data of the first sample, which had been stained for both DNA and HER-2/neu. Sparsely growing AU-565 cells were used for calibrating the HER-2/neu protein content. The level of staining in such cells was defined as 100%. A complete description of this quantification is available in Bacus S., et al., "HER-2/neu Oncogene Expression and DNA Ploidy Analysis in Breast Cancer," *Arch. Pathol. Lab. Med.*, Vol. 114, pp. 164–169, February 1990.

Cell numbers were determined by hemocytometer chamber counting, and viability was monitored by trypan blue dye exclusion.

According to the method of treatment and analysis described above, the N29 antibody was found to be the best differentiation inducer. Treatment of AU-565 cells for four days with 10 μg/mL N29 antibody doubled the proportion of cells with flat morphology, and increased the nuclear area of the cells on average to 154 μm² over the control cell nuclear area of 100 μm². The fraction of morphologically mature AU-565 cells increased from 10–20% in the untreated cells to more than 90% in the cells treated with N29 antibody. The fraction of 565 cells treated with N29 antibody which contained lipid droplets was 55%, compared to 12% in the untreated control. The fraction of N29-treated AU-565 cells staining positively for the presence of casein after four days was more than 90%, compared to 20% for the untreated control. The population of N29-treated AU-565 cells was $4.8 \times 10^4$ per square centimeter after four days, compared with $6 \times 10^4$ untreated cells.

Incubation of AU-565 cells with N29 antibody resulted in a decrease in membrane staining for HER-2/neu which was accompanied by diffuse cytoplasmic localization of the protein. Quantification of the staining revealed that the redistribution involved a transient increase in total cellular HER-2/neu content.

Confocal microscope images confirmed the immunohistochemical staining results. The protein migrated from the membrane and localized in the cytoplasm and in particular the perinucleus upon treatment with N29 antibody.

Treatment of MDA-MB 453 cells with N29 antibody (data not shown) elicited a marked growth inhibition of 60%, and an increase in cells positive for differentiation markers: 90% of treated cells stained positively for lipid droplets, and 70% of treated cells stained positively for casein. Treatment of MCF-7 cells with N29 antibody (data not shown) increased the fraction containing lipid droplets and casein to about 90%, compared with 2% in the untreated control portion. N29 had only a small growth inhibition effect on MCF-7 cells.

EXAMPLE II

Cells of the AU-565 cell line were treated with 1 μg/ml, 3 μg/ml and 10 μg/ml of the N12, N24, N28 or N29 antibodies for a period of four days as described in Example I. An unrelated IgG (10 μg/ml) was used as a control. Staining for lipid droplets, casin, and HER-2/neu, as well as quantification of HER-2/neu by optical density values and determination of localization of the protein were also carried out as in Example I.

Ther results are shown in Table II:

TABLE II

| CELL GROWTH, DIFFERENTIATION MARKERS AND HER-2/NEU LEVELS IN AU-565 CELLS TREATED FOR FIVE DAYS | | | | | |
|---|---|---|---|---|---|
| Treatment | Concentration μg/ml | Cell Numbers $10^4$/cm² | HER-2/neu percent* | Nuclear Area μm² | % Cells stain for lipid droplets |
| Control |  | 6.2 | 89% | 115.0 | 28 |
| IgG | 10 | 6.1 | 95% | 117.4 | 19 |
| N29 | 1 | 4.8 | 119% | 144.2 | 53 |
| N12 | 1 | 6.0 | 85% | 101.3 | 18 |
| N24 | 1 | 5.6 | 102% | 136.0 | 48 |
| N28 | 1 | 6.1 | 86% | 114.7 | 31 |
| N29 | 3 | 4.1 | 136% | 166.5 | 72 |
| N12 | 3 | 5.5 | 90% | 119.4 | 38 |
| N24 | 3 | 4.9 | 105% | 156.1 | 57 |
| N28 | 3 | 7.4 | 101% | 119.0 | 22 |
| N29 | 10 | 3.6 | 124% | 167.2 | >90 |
| N12 | 10 | 5.3 | 104% | 117.3 | 61 |
| N24 | 10 | 4.4 | 95% | 156.6 | 69 |
| N28 | 10 | 8.0 | 117%# | 119.7 | 17 |

*HER-2/neu in sparsely growing untreated AU-565 = 100%
Confluent Conditions

Again, N29 antibody showed the best efficacy in inducing differentiation. The N29 antibody preparation demonstrated a dose-dependent differentiation-inducing effect at concentrations as low as 1 μg/ml. Again, sparsely growing AU-565 cells were used for calibrating the level of HER-2/neu in the cells. The level of staining in these cells was defined as 100%.

EXAMPLE III

Human breast cancer cell line AU-565 was cultured as in Example I above, and incubated with the widely available murine TA-1 (IgG) monoclonal antibody from DuPont Corp., which reacts with the extracellular ligand binding domain of the human HER-2/neu protein (and may also be used as described above in staining for membrane-bound HER-2/neu after fixation). Incubation with the TA-1 monoclonal antibody was initiated 24 hours after cell inoculation. From 15%–20% of the cells in the control cultures exhibited a mature phenotype, characterized by large, lacy nuclei, and a spread cytoplasm containing sizable lipid droplets. Incubation of AU-565 cells for 2 days with 1 μg/Ml TA-1 resulted in a three dimensional pattern of cell growth with an increased fraction of cells having mature phenotype. On the fourth day, the number of cells in the treated portion decreased by 60% relative to the control, and the fraction of mature cells increased from the range of 15%–20% to the range of 50%–60%.

Immunohistochemical staining for casein and lipid droplets was performed as in Example I. Cell numbers were determined by hemocytometer chamber counting. Results are shown in Table III:

TABLE III

CELL GROWTH AND DIFFERENTIATION MARKERS IN AU-565 BREAST CANCER CELLS AFTER FOUR DAYS OF TREATMENT WITH TA-1

| Treatment | Concentration μg/ml | Cells with lipid droplets (percent) | Cell Numbers ($10^4/cm^2$) | Nuclear Area ($\mu m^2$) |
|---|---|---|---|---|
| Control | 0.0 | 23% | 5.7 | 100 |
| IgG | 1.0 | 16% | 5.1 | 96 |
| TA-1 | 0.5 | 33% | 3.0 | 156 |
| TA-1 | 1.0 | 48% | 2.3 | 160 |

EXAMPLE IV

A 30 kiloDalton factor called gp30 secreted from MDA-MB-231 human breast cancer cells has been shown to be a ligand for the HER-2/neu receptor, a 185 kiloDalton transmembrane receptor (also known as P185$^{HER-2/neu}$) encoded by the HER-2/neu oncogene.

A method for isolating gp30 is described in Lupu, R., et al, "Direct Interaction of a Ligand for the erbB2 Oncogene Product with the EGF Receptor and p185erbB2," Science, Vol. 249, pp. 1552–1555 (1990). Briefly, gp30 may be isolated from the conditioned media of MDA-MB-231 cells low-affinity chromatography on a heparin-Sepharose column. Fractions containing active gp30 may be detected by the ability of gp30 to bind to epidermal growth factor receptor (EGFR) on the cell membranes of A431 cells or MCF-7 cells (which cells are well known and publicly available). Fractions containing gp 30 activity which are obtained after heparin-Sepharose chromatography may be then chromatographed by reversed-phase chromatography on a μBondapak $C_3$ column equilibrated in 0.05% trifluoroacetic acid and eluted with a steep gradient of acetonitrile and then rechromatographed, in a second round of reversed-phase chromatography on the μBondapak $C_3$ column (equilibrated in 0.05% trifluoroacetic acid), where elution is with a narrow gradient of cetonitrile. Ligand gp30 elutes at a 25 to 30% acetonitrile gradient.

The gp30 used in this Example were dissolved in PBS and filtered. The protein concentration of the ligand solution was confirmed after the filtration step.

Malignant breast cells of each of the three cell lines, AU-565, MDA-MB453 and MCF-7, were seeded and cultured as described in Example I. The culture media was supplemented with 0.0, 0.3 or 6.0 ng/ml of ligand gp30 (kindly supplied by Dr. Ruth Lupu of Vincent Lombardi Cancer Center, Georgetown University, Washington, D.C.) instead of the monoclonal antibody preparations. The methods for determining the presence of lipid droplets, casein, and quantification of HER-2/neu protein were all carried out as described in Example I.

Treatment of AU-565 cells with various doses of gp30 inhibited cell growth in a dose-dependent fashion, in the nanogram range. Treatment of AU-565 cells with 6 ng/ml for four days resulted in about 40% growth inhibition. Treatment of MDA-MB 453 cells for four days with 6 ng/ml of the ligand gp30 resulted in 42% growth inhibition compared to the untreated control. Similar treatment of MCF-7 cells resulted in no inhibition of growth. These results are shown in Table IV.

TABLE IV

CELL GROWTH AND DIFFERENTIATION MARKERS IN BREAST CANCER CELLS AFTER FOUR DAYS OF TREATMENT WITH gp30

| Concentration ng/ml | Cells with lipid droplets (percent) | Cell Numbers ($10^4/cm^2$) | Nuclear Area ($\mu m^2$) |
|---|---|---|---|
| AU-565 Cells | | | |
| 0.0 | 15 | 4.0 | 96.0 |
| 0.3 | 28 | 5.3 | 162.0 |
| 6.0 | 76 | 2.4 | 204.0 |
| MDA-MB 453 Cells | | | |
| 0.0 | 20 | 3.4 | 65.3 |
| 0.3 | 62 | 2.9 | 77.8 |
| 6.0 | 84 | 2.0 | 113.1 |
| MCF-7 Cells | | | |
| 0.0 | <1 | 11.0 | 252.0 |
| 0.3 | <2 | 11.0 | 251.0 |
| 6.0 | 5 | 11.0 | 277.0 |

At the time of treatment, about 7% of AU-565 cells, 10% of MDA-MB 453 cells, and less than 1% of MCF-7 cells contained small lipid droplets. Treatment of AU-565 cells for 4 days with 6 ng/ml gp30 increased the fraction of cells having lipid droplets to 76%, whereas 15% of the control cells had lipid droplets. With respect to MDA-MB 453 cells, treatment for four days with 6 ng/ml gp30 increased the percentage of cells exhibiting lipid droplets to 84%, whereas 20% of the control cells exhibited lipid droplets. Similar treatment of MCF-7 cells (which do not express HER-2/neu) resulted in at most about 5% of the cells exhibiting lipid droplets, while less than 1% of control MCF-7 cells (0.0 ng/ml gp30) exhibited lipid droplets.

AU-565 cells were also treated with gp30 at concentrations less than 1 ng/ml. Surprisingly, treatment of these cells with a very low dose of gp30, less than 1 ng/ml, resulted in stimulation of cell growth, as can be seen in FIG. 1. This data is shown in Table V:

TABLE V

CELL GROWTH AND DIFFERENTIATION MARKERS IN AU-565 CELLS AFTER 6 DAYS OF TREATMENT WITH gp30

| Concentration ng/ml | Cells with lipid droplets (percent) | Cell Numbers ($10^4/cm^2$) | Nuclear Area ($\mu m^2$) |
|---|---|---|---|
| 0.00 | 17 | 8 | 94 |
| 0.03 | 14 | 19.3 | 93 |
| 0.1 | 16 | 12.6 | 101 |

TABLE V-continued
CELL GROWTH AND DIFFERENTIATION MARKERS IN AU-565 CELLS AFTER 6 DAYS OF TREATMENT WITH gp30

| Concentration ng/ml | Cells with lipid droplets (percent) | Cell Numbers ($10^4/cm^2$) | Nuclear Area ($\mu m^2$) |
| --- | --- | --- | --- |
| 0.3 | 27 | 9.6 | 162 |
| 1.0 | 46 | 7.5 | 180 |
| 3.0 | 76 | 4.6 | 206 |
| 6.0 | >90 | 2.3 | 236 |

Cells not treated with gp30 attained a cell density after six days of approximately $8 \times 10^4/cm^2$. The results show that maximum growth stimulation occurs at a ligand concentration of about 0.03 ng/ml for gp30, where a cell density of about $1.93 \times 10^5/cm^2$ is attained. Thus, very low concentrations of gp30 appear to agonize malignant cell growth in cells which overexpress HER-2/neu.

With respect to inducing terminal cell differentiation in malignant cells expressing or overexpressing HER-2/neu, more than 90% of AU-565 cells treated with 6 ng/ml gp30 for 6 days evidenced mature morphology. Treatment of AU-565 cells for 6 days with 6 ng/ml gp30 increased the fraction of cells having lipid droplets to over 90% (control=24%). Under identical treatment conditions, the percentage of cells staining positively for casein increased to 90% (control=30%).

Unlike AU-565, MCF-7 cells (which do not express HER-2/neu) treated with 6 ng/ml gp30 did not show marked morphological differences compared to untreated cells.

As with induction of terminal differentiation by monoclonal antibodies specific for the extracellular domain of the HER-2/neu protein, induction of terminal differentiation by the ligand gp30 resulted in translocation of HER-2/neu protein from the membrane to the cytoplasm and perinuclear region of the cell.

Figure 2:
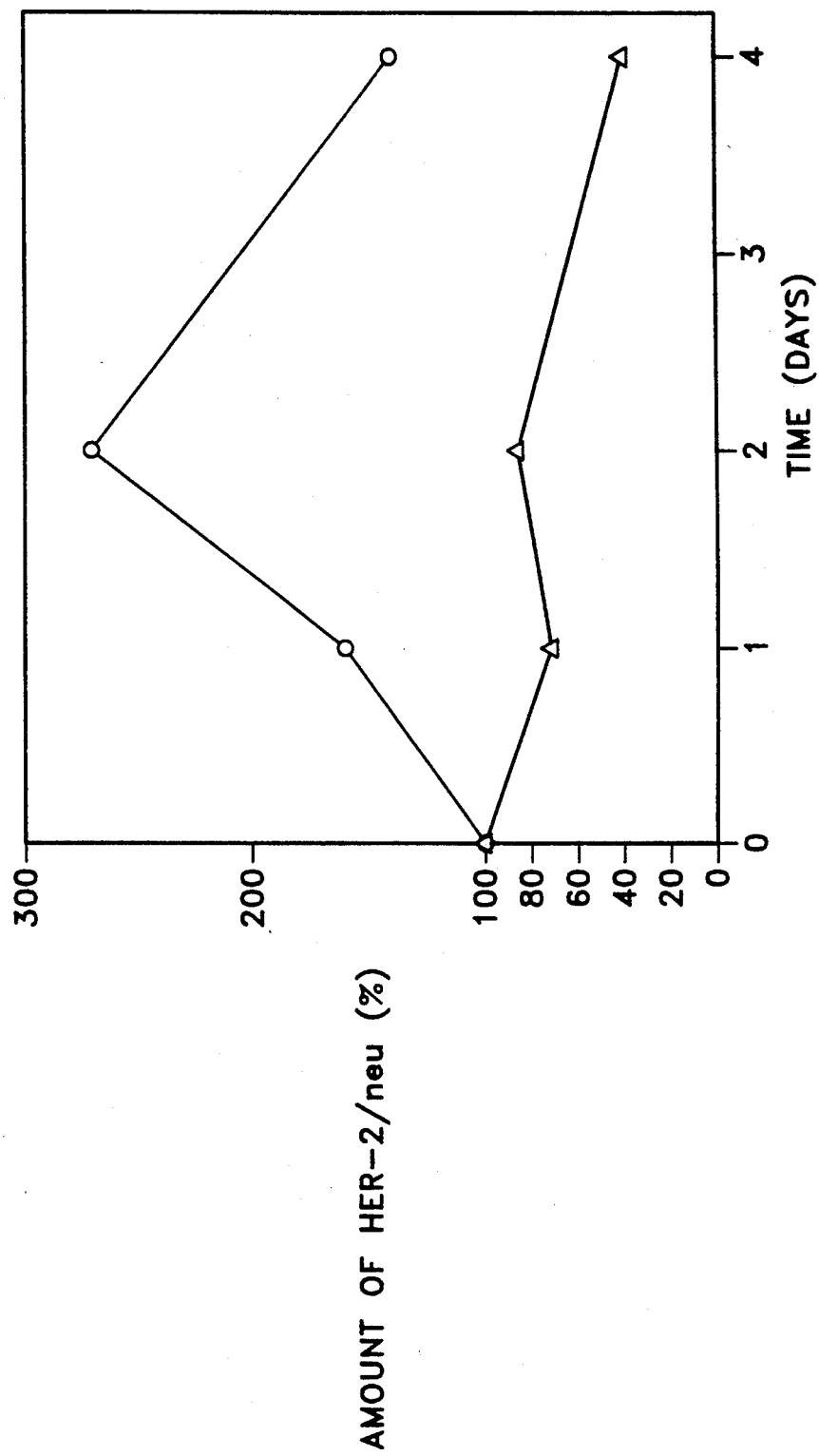
FIG. 2 shows a graph of total cellular HER-2/neu content in AU-565 cells over time as quantified by immunohistochemical stain optical density analysis. Open triangles represent a control sample, while open circles represent a sample treated with 6 ng/ml of ligand gp30 for six days.

During four days in cultures, the cell surface of 80-90% of untreated AU-565 cells reacted with the antibody to the HER-2/neu protein, as shown by immunostaining as described in the previous Examples. The remaining cells, which had the morphology of mature cells, showed reduced membrane staining and diffuse cytoplasm staining. Treatment of AU-565 cells with concentrations of gp30 which inhibited growth and induced differentiation markers (over 1 ng/ml) caused a time dependent decrease in membrane staining, and a transient increase in total cellular HER-2/neu staining and cytoplasmic staining, as can be seen in FIG. 2. This diffuse immunostaining increased two- to three-fold during the initial two days of treatment, and decreased in the following two days.

However, treatment of AU-565 cells with 0.03-1 ng/ml gp30 did not change the immunostaining pattern of HER-2/neu, which remained mainly membranous.

The immunostaining for HER-2/neu in MDA-MB 453 cells was less intense, yet the pattern and kinetics of staining, after a similar treatment, were similar to those observed in AU-565.

These results indicate that treatment of breast cancer cells with the ligand gp30, either inhibited or accelerated breast cancer cell growth, depending on the concentration of the ligand. Ligand concentrations which resulted in cell growth inhibition induced cellular responses that resulted in cell differentiation and acquisition of mature phenotype, which was associated with translocation of the HER-2/neu protein from the membrane to the perinuclear area.

EXAMPLE V

Two human breast cancer cell lines, AU-565 and MCF-7, were treated with the chemicals mycophenolic acid (MPA), phorbol 12-myristate 13-Acetate (PMA), or retinoic acid (RA), which are known to induce maturation at low concentrations in a variety of human cells types. The cells were cultured as in Example I. Cells were inoculated into either Lab-tech four chamber slides from Nunc, Inc., Naperville, Ill., at $0.5 \times 10^4$ or $2 \times 10^5$ cells in 1 mL of medium per chamber or into 100 mm petri dishes at $5 \times 10^4$ cells in 10 mL of medium.

PMA and RA were dissolved in dimethylsulfoxide and stored at $-70°$ Celsius. MPA was dissolved in 150 MM NaHCO3. Treatment with MPA, PMA, or RA was initiated 48 hours after cell inoculation. Sparse cultures of the two cell lines were treated for four days with 9 $\mu$M MPA, 1.6 nM PMA, or 2.5 $\mu$M RA.

Four measures of cell differentiation were used. These include cell proliferation, morphological change, expression of phenotype, and migration of HER-2/neu from the cell surface to cytoplasm. The results are shown in Table VI:

TABLE VI
CELL GROWTH AND DIFFERENTIATION MARKERS IN AU-565 AND MCF-7 CELLS AFTER 4 DAYS OF TREATMENT WITH MPA, PMA OR RA

| Treatment | Concentration $\mu$g/ml | Cells with lipid droplets (percent) | Cell Numbers ($10^4/cm^2$) | Nuclear Area ($\mu m^2$) |
| --- | --- | --- | --- | --- |
| AU-565 cells | | | | |
| Control | 0.0 | 14% | 6.0 | 80 |
| MPA | 9.0 $\mu$M | 63% | 1.0 | 200 |
| PMA | 1.6 nM | 67% | 0.8 | 285 |
| RA | 2.5 $\mu$M | 97% | 2.1 | 220 |
| MCF-7 cells | | | | |
| Control | 0.0 | <1% | 15.0 | 170 |
| MPA | 9.0 $\mu$M | 5% | 2.7 | 163 |
| PMA | 1.6 nM | 6% | 12.5 | 167 |
| RA | 2.5 $\mu$M | 1% | 7.2 | 166 |

Cell proliferation was determined by counting cells in a hemocytometer chamber. The cell count was monitored over four days.

Qualitative morphological appearance also characterized differentiation. Analysis of cell morphology in control cultures indicated that 70-80% of untreated, sparsely growing AU-565 cells had the morphology of immature cells, characterized by compact nuclei enclosed by a fine layer of cytoplasm. Another 10-20% displayed a morphology associated with mature cells, having large and lacy nuclei surrounded by sizeable flat cytoplasms. Treatment of this cell line with MPA increased the fraction of morphologically mature cells to about 60%, while treatment with PMA or RA increased this fraction to more than 90%. Untreated or treated MCF-7 cells did not show marked differences in their morphological appearance.

Phenotype expression as a marker of terminal cell differentiation was measured by detecting the production of lipid droplets and casein, both of which are components of human milk. Lipid droplets were detected by a modify "Oil Red O in propylene glycol" method, as described in previous Examples.

The presence of casein was detected by histochemical staining with a human antibody to human casein kindly supplied by Dr. J. Koistinen of the Finnish Red Cross Transfusion Service in Helsinki, Finland.

At the time of treatment, about 5% of the cells in the sparse AU-565 cultures and less than 1% of the cells in the MCF-7 cultures contained small lipid droplets. Treatment of AU-565 cultures with MPA or PMA increased the fraction of cells containing the lipid droplets in a time dependent manner to 60-70%. Treatment with RA increased this fraction to more than 90%. Moreover, the lipid droplets in the treated cells were visibly larger than those observed in untreated cells by more than five-fold.

Unlike the AU-565 cells, the MCF-7 cultures treated with MPA, PMA, or RA showed only a small increase in the fraction of cells containing the large lipid droplets: up to about 5% of the cells in cultures treated with MPA or PMA and little or no increase over controls in cultures treated with RA.

Four days after treatment of the two cell lines was begun, the control cultures contained less than 2% of cells that reacted positively with the anti-casein antibody. Treatment of AU-565 cultures with either MPA or RA increased this to 70 to 80%, and treatment with PMA to about 90%. Treatment of the MCF-7 cultures with MPA or RA also increased the percentage of cells staining positively for casein. PMA, even at high doses, had little or no effect on the MCF-7 cell fractions staining positively for this milk protein.

The HER-2/neu protein was detected by specific antibodies, as described in Example I, and translocation and quantification were performed as also described in Example I.

During four days in culture, the cell surface membrane of 80-90% of untreated AU-565 cells reacted with the two antibodies. The remaining cells, which had the morphology of mature cells, showed reduced membrane staining but increased diffusive cytoplasmic immunostaining. Treatment of AU-565 cells with MPA, PMA, or RA caused a time dependent decrease in cell surface membrane concentration of HER-2/neu, and a two- to three-fold increase in cytoplasmic concentration of the protein. The immunostaining in the untreated MCF-7 cells was about one-tenth that in untreated AU-565 cells. However the pattern and kinetics of immunostaining after treatment with MPA or RA were similar to those observed for AU-565 cells. PMA, which did not induce differentiation markers in the MCF-7 cells, did not cause a change in the pattern of immuno staining with these antibodies.

Thus, the methods of the present invention provide a powerful prognostic tool for predicting the effectiveness of a cancer therapy using monoclonal antibodies or ligands which induce differentiation of cancer cells. The methods of the present invention also provide for the screening of putative anti-cancer agents for the determination of efficacy of the agent in treatment of a malignancy. Monoclonal antibodies and ligands identified in accordance with the present invention induce the expression of mature phenotype and terminal cell differentiation, thereby inhibiting the growth of a malignancy. Additionally, the methods of the invention provide for the determination of beneficial doses of, and/or improved combinations of, such therapeutic agents. Finally, the methods of the present invention are easily performed, and are therefore time- and cost-effective, as well as minimally traumatic to a cancer patient.

While the invention has been described with some specificity, modifications apparent to those with ordinary skill in the art may be made without departing from the scope of the invention.

Various features of the invention are set forth in the following claims.

What is claimed is:

1. A method for determining/prognosticating the effectiveness of a therapeutic agent in the treatment of a cancer by measuring the ability of the therapeutic agent to induce terminal cell differentiation wherein malignant cells of the cancer overexpress an oncogene product, the method comprises the steps of:
    (a) obtaining from a human having such a cancer a biopsy comprising viable malignant cells which overexpress at least one oncogene product and dividing the same into first and second portions;
    (b) treating the first portion comprising viable cells with a sufficient quantity of a composition comprising at least one compound having specific binding affinity for the oncogene product and contacting the second portion with a composition which is devoid of the at least one compound having specific binding affinity for the oncogene product;
    (c) maintaining the first and second portions in a physiologically acceptable medium for an amount of time sufficient to induce maturation in the viable malignant cells of said first portion: and
    (d) comparing the percentage of cells in the first portion which exhibit markers of terminal cell differentiation to the percentage of cells in the second portion which exhibit markers of terminal cell differentiation wherein effectiveness of treatment correlates with the degree of terminal cell differentiation.

2. A method according to claim 1 wherein the biopsy comprises viable malignant cells which overexpress on their surface membrane at least one oncogene product.

3. A method according to claim 2 wherein the oncogene product is a receptor and the compound having specific binding affinity is specific for a segment extracellular domain of the receptor which affects the receptor.

4. A method according to claim 3 wherein the receptor is HER-2/neu protein.

5. A method according to claim 4 wherein terminal cell differentiation is determined by translocation of HER-2/neu from the cell surface membrane to the cytoplasm or perinuclear region of the cell.

6. A method according to claim 5 wherein translocation of HER-2/neu is determined immunohistochemically with an antibody which is specific for the HER-2/neu protein.

7. A method according to claim 4 wherein said cancer is breast cancer and terminal cell differentiation is determined by production of a human milk components.

8. A method according to claim 7 wherein the milk component is casein.

9. A method according to claim 7 wherein the milk component is lipid droplets.

10. A method for determining/prognosticating the effectiveness of a therapeutic agent in the treatment of a cancer by measuring the ability of the therapeutic agent to induce terminal cell differentiation wherein malignant cells of the cancer overexpress an oncogene product, the method comprising the steps of:
    (a) obtaining from a human having such a cancer a biopsy comprising viable malignant cells which overexpress at least one oncogene product and dividing the same into first and second portions;

(b) treating the first portion comprising viable cells with a sufficient quantity of a composition comprising at least one compound having specific binding affinity for the oncogene product and contacting the second portion with a composition which is devoid of the at least one compound having specific binding affinity for the oncogene product;

(b) maintaining the first and second portions in a physiologically acceptable medium for an amount of time sufficient to induce maturation in the viable malignant cells of said first portion: and (d) comparing a quantification of the average cellular amount of said oncogene product across the cells in the first portion to a quantification of the average cellular amount of said oncogene product across the cells in the second portion.

11. A method according to claim 10 wherein the biopsy comprises viable malignant cells which overexpress on their surface membrane at least one oncogene product.

12. A method according to claim 11 wherein the oncogene product is a receptor and the compound having specific binding affinity is specific for a segment extracellular domain of the receptor which affects the receptor.

13. A method according to claim 12 wherein the receptor is HER-2/neu protein.

14. A method according to claim 13 wherein quantification of HER-2/neu is determined by measurement of optical density in cells stained immunohistochemically with an antibody which is specific for the HER-2/neu protein.

15. A method according to claim 14 wherein only membrane-bound HER-2/neu is quantified.

16. A method according to claim 14 wherein only cytoplasmic HER-2/neu is quantified.

17. A method according to claim 14 wherein the total amount of HER-2/neu in a cell is quantified.

* * * * *